(12) United States Patent
Larsen et al.

(10) Patent No.: US 11,052,185 B2
(45) Date of Patent: Jul. 6, 2021

(54) MEDICAL INJECTION DEVICE HAVING A SEALABLE CLEANING RESERVOIR

(71) Applicant: Novo Nordisk A/S, Bagsvaerd (DK)

(72) Inventors: Bjoern Gullak Larsen, Birkeroed (DK); Christian Plambech, Soeborg (DK); Lars Eilertsen, Fredensborg (DK); Mattias Ingerslev, Copenhagen OE (DK); Ruben Archilla, Copenhagen NV (DK); Soeren Dyring Jensen, Valby (DK)

(73) Assignee: Novo Nordisk A/S, Bagsvaerd (DK)

( * ) Notice: Subject to any disclaimer, the term of this patent is extended or adjusted under 35 U.S.C. 154(b) by 408 days.

(21) Appl. No.: 15/757,931

(22) PCT Filed: Sep. 19, 2016

(86) PCT No.: PCT/EP2016/072164
§ 371 (c)(1),
(2) Date: Mar. 6, 2018

(87) PCT Pub. No.: WO2017/050694
PCT Pub. Date: Mar. 30, 2017

(65) Prior Publication Data
US 2018/0339098 A1   Nov. 29, 2018

(30) Foreign Application Priority Data
Sep. 22, 2015   (EP) ..................... 15186192

(51) Int. Cl.
*A61M 5/00* (2006.01)
*A61M 5/32* (2006.01)
(Continued)

(52) U.S. Cl.
CPC .............. *A61M 5/001* (2013.01); *A61M 5/24* (2013.01); *A61M 5/2466* (2013.01);
(Continued)

(58) Field of Classification Search
CPC .. A61M 5/001; A61M 5/3243; A61M 5/3245; A61M 5/321; A61M 5/3205;
(Continued)

(56) References Cited

U.S. PATENT DOCUMENTS

| 3,354,881 A | 11/1967 | Bloch |
| 4,416,663 A | 11/1983 | Hall |

(Continued)

FOREIGN PATENT DOCUMENTS

| CN | 104768598 A | 7/2015 |
| CN | 106456903 A | 2/2017 |

(Continued)

*Primary Examiner* — Amber R Stiles
*Assistant Examiner* — Alexandra Lalonde
(74) *Attorney, Agent, or Firm* — Wesley Nicolas (57) ABSTRACT

The present invention concerns a medical injection device for apportioning set doses of a preservative containing liquid drug. The injection device comprises a housing supporting a cartridge containing the preservative containing liquid drug and a needle cannula for transferring the liquid drug from the cartridge and through the skin of a user. Further, a needle shield which is axially movable in relation to the housing is also present. The axially movable shield carries a cleaning reservoir for cleaning at least the tip of the needle cannula between subsequent injections and the cleaning reservoir is preferably filled with preservative containing liquid drug directly from the cartridge upon initiation of the injection device. In order to eliminate any overpressure being built up inside the cleaning reservoir during the filling process, the cleaning reservoir is provided with an outlet configured to be permanently sealed by a user activated operation.

26 Claims, 8 Drawing Sheets

(51) Int. Cl.
*A61M 5/24* (2006.01)
*A61M 5/20* (2006.01)

(52) U.S. Cl.
CPC .......... *A61M 5/3202* (2013.01); *A61M 5/326* (2013.01); *A61M 5/3257* (2013.01); *A61M 5/2033* (2013.01); *A61M 2005/3267* (2013.01)

(58) Field of Classification Search
CPC ........ A61M 5/32; A61M 5/24; A61M 5/2429; A61M 5/3202; A61M 5/3257; A61M 5/2466; A61M 5/326; A61M 5/2033; A61M 5/20; A61M 5/31; A61M 2005/3267; A61M 2005/2006; A61M 2005/2013; A61M 2005/206; A61M 2005/3117; A61M 2005/3118; A61M 2005/312; A61M 2209/10
See application file for complete search history.

(56) References Cited

U.S. PATENT DOCUMENTS

| 4,507,118 A | 3/1985 | Dent |
| 4,666,436 A | 5/1987 | McDonald et al. |
| 4,769,026 A | 9/1988 | Strung |
| 2017/0136173 A1 | 5/2017 | Melander et al. |

FOREIGN PATENT DOCUMENTS

| EP | 182682 A1 | 5/1986 | | |
| WO | 2014029018 A1 | 2/2014 | | |
| WO | 2014064100 A1 | 5/2014 | | |
| WO | WO-2014064100 A1 * | 5/2014 | .......... | A61M 5/3257 |
| WO | 2015062845 A1 | 5/2015 | | |
| WO | WO-2015062845 A1 * | 5/2015 | ............ | A61M 5/326 |
| WO | 2015/101487 A1 | 7/2015 | | |
| WO | 2015/117854 A1 | 8/2015 | | |
| WO | 2015/124410 A1 | 8/2015 | | |
| WO | 2015173151 A1 | 11/2015 | | |

\* cited by examiner

MEDICAL INJECTION DEVICE HAVING A SEALABLE CLEANING RESERVOIR

CROSS-REFERENCE TO RELATED APPLICATIONS

This application is a 35 U.S.C. § 371 National Stage application of international Application PCT/EP2016/072164 (published as WO 2017/050694), filed Sep. 19, 2016, which claims priority to European Patent Application 15186192.9, filed Sep. 22, 2015, the contents thereof which are incorporated by reference in their entirety.

THE TECHNICAL FIELD OF THE INVENTION

The invention relates to a medical injection device having a shielded needle cannula. The invention especially refers to such an injection device wherein the shielded needle cannula is provided for repeated use and the distal tip of the needle cannula penetrating into the skin of the user during injection is cleaned between subsequent injections.

DESCRIPTION OF RELATED ART

Injection devices wherein the tip of the needle cannula is maintained in a cleaning solvent between subsequent injections are disclosed in U.S. Pat. Nos. 3,354,881, 4,416,663 and WO 2014/064100. As can be seen from these prior art injection devices, the cleaning chamber or reservoir is usually carried distally on a retractable shield covering the tip of the needle cannula between subsequent injections.

WO 2014/064100 discloses a pre-filled disposable injection device which has a axially movable shield covering the distal tip of the needle cannula between subsequent injections. This axially movable shield is urged into a distal covering position by a spring. Further, in one embodiment, the axially movable shield is provided with a hollow chamber containing a liquid solvent such as a chemical disinfectant or biocide which cleans the tip of the needle cannula between subsequent injections. Examples on such cleaning solvents are provided in WO 2014/029018.

WO 2015/062845 discloses the possibility of using the liquid medical drug contained inside the cartridge as a cleaning solvent. This requires that the liquid drug contains a preservative which is often the case. In one embodiment the cleaning reservoir is filled with liquid drug directly from the cartridge of the injection device by the user when initiating first use. However, the cleaning reservoir could also be filled by the manufacture.

Between subsequent injections, the distal tip of the needle cannula is maintained inside the cleaning reservoir and the proximal part is maintained inside the cartridge. The liquid system thus comprises the cleaning reservoir, the lumen of the needle cannula and the interior of the cartridge.

The cleaning reservoir can either have a variable volume as disclosed in WO2015/062845 or the volume can be fixed as disclosed in WO 2015/173151. In either case when transferring a volume of the preservative containing liquid drug from the cartridge and into the cleaning reservoir the volume transferred can sometime be larger than the volume of the cleaning reservoir which results in an overpressure being created inside the liquid system which can lead to inaccurate dose expelling, especially when taking the first injection. In WO2015/173151 this is solved by connecting the cleaning reservoir to an overflow chamber or simply just to the surroundings.

When the cleaning reservoir is connected to the surroundings, any air trapped inside the cleaning reservoir is also allowed to escape as the cleaning reservoir is being filled with liquid drug. However, when the cleaning reservoir is connected to the surroundings bacteria can enter into the cleaning reservoir.

DESCRIPTION OF THE INVENTION

It is thus an object of the present invention to provide an injection device with a cleaning reservoir and wherein the injection device is able to prevent any permanent build-up of overpressure in the liquid system and especially in the cleaning reservoir by automatically equalizing any overpressure occurring during filing of the cleaning reservoir prior to making the first injection.

It is further an object to prevent bacteria entering into the cleaning reservoir after the cleaning reservoir has been filled.

The invention is defined in claim 1. Accordingly in one aspect the present invention relates to a medical injection device by which a user can apportion set doses of a liquid drug to a user, preferably by self-injection. The medical injection device comprises:

- A housing which supports a cartridge e.g. made from glass and which contains the preservative containing liquid drug to be injected.
- A needle cannula, preferably made from stainless steel and which needle cannula has a distal part and a proximal part with a longitudinal lumen. The needle cannula is preferably grinded at the distal end to form a sharp tip for penetrating the skin of the user and is mounted relatively to the housing such that the distal part extend in a distal direction and the proximal part extend in a proximal direction and into the cartridge at least during injection.
- An axially movable shield which is telescopically movable in relation to the housing from a first extended position to a second retracted position. The axially movable shield carries a cleaning reservoir which distally is sealed by a distal pierceable seal and proximally sealed by a proximal pierceable seal. The two seals are longitudinal spaced from each other to form the cleaning reservoir and the cleaning reservoir contains an amount of the preservative containing liquid drug present in the cartridge.

In the first extended position, the distal tip of the needle cannula is maintained located inside the cleaning reservoir, and in the second position the axially movable shield is moved proximally to uncover the distal tip which thus in the second position is located distal to the cleaning reservoir.

The cleaning reservoir is further provided with an outlet such that the preservative containing liquid drug can escape from the cleaning reservoir during filling of the cleaning chamber and with means for sealing the outlet such that further preservative containing liquid drug is prevented from escaping from the cleaning reservoir.

When the cleaning reservoir is being filled with preservative containing liquid directly from the cartridge an overpressure will often be created in the liquid system and particular inside the cleaning reservoir as there may be a surplus of preservative containing liquid drug inside the cleaning reservoir due to various tolerances in the injection device. In order to eliminate this overpressure an outlet is provided through which air and drug can escape during filling of the cleaning reservoir. However, when using the injection device for further subsequent injections it is important to seal off the outlet after filling of the cleaning reservoir such that the drug filled into the cleaning reservoir remains inside the cleaning reservoir for further use as a cleaning solvent.

It is therefore necessary to have sealing means which can seal off the outlet from the cleaning reservoir once the reservoir has been filled and the overpressure has been equalized.

These sealing means can be envisage in a number of different ways whereof some particular embodiments will be explained in the following The sealing means are preferably configured to be sealed by a user activated operation. In order to permanently seal off the outlet from the cleaning reservoir after initiation the present invention suggest having sealing means which is activated to seal the outlet from the cleaning reservoir upon and in response to the first use of the injection device.

In one embodiment the cleaning reservoir is configured as a tube like structure which is distally sealed by a distal pierceable seal and proximally sealed by a proximal pierceable seal and which tube structure is carried by the axially movable shield. In this way the closing of the outlet can be coupled to the axial movement of the axially movable shield.

The outlet leading air and any surplus of liquid drug away from the cleaning reservoir can either lead into a chamber or directly out to the surroundings. When leading to the surroundings an additional sterile barrier can be provided In one example, the outlet is in liquid communication with an overflow chamber and both the outlet and the overflow chamber are provided as a removable part coupled to the axially movable shield. The removable part can in one example be a cover the user is required to remove before making the first injection. Upon removable of the cover the user thus also removes both the outlet and the overflow chamber thereby sealing off the cleaning reservoir. In a preferred example the removable part is formed as a part of the protective cap for the injection device.

The connection between the cleaning reservoir and the overflow chamber is preferably formed by a tube having a lumen which can be closed or otherwise sealed in response to the user performing an action leading to the filling of the cleaning reservoir.

In a further embodiment, either the distal pierceable seal or the proximal seal is removed a distance (Y) from the tube when the injection device is un-used. The action of making the initial injection i.e. press the telescopically needle shield against the skin of the user, makes the seal move relatively to the tube forming the cleaning reservoir. This movement closes the open distance (Y) and thus seals the cleaning reservoir. The pierceable seal to be moved is preferably carried by an axially movable element thus introducing and guiding an axial movement of the pierceable seal to be moved.

In a further embodiment, the sealing of the cleaning reservoir is a result of a rotatable movement.

The cleaning reservoir is preferably connected to an overflow channel by a radial opening. The overflow channel can either form a closed compartment or it can lead directly to the surroundings.

The radial opening can in this further example be sealed by operating a seal element which preferably by a user operation can be brought to a position in which it seals the radial opening thus sealing the cleaning reservoir.

In one example, the cleaning reservoir is surrounded by the seal element which by a relative rotation between the cleaning reservoir and the seal element can be brought to the sealed position. It is thus possible to close and seal the radial opening by rotating the seal element relatively to the radial opening or vice versa.

Further, the needle cannula is mounted in a hub which is either permanently or releasable connected to the injection device and the seal element is rotatable inserted between the hub and the tube forming the cleaning reservoir. Further, in an example, the hub has a configuration forcing the seal element to rotate relatively to the tube during the first axial movement. Once the seal element has been moved once (axially and rotational) it is continued to move strictly axially upon further injections. It thus seals off the radial opening when moved helically during the initial operation of the injection device.

In another example, the seal element is maintained rotational fixed to the housing and the tube structure making up the cleaning reservoir is rotated when initiating the injection device. During this rotation the radial opening is rotated into a position wherein it is aligned with a seal structure provided inside the seal element. This seal structure is preferably an elastomer provided on the inner surface of the seal element.

DEFINITIONS

An "injection pen" is typically an injection apparatus having an oblong or elongated shape somewhat like a pen for writing. Although such pens usually have a tubular cross-section, they could easily have a different cross-section such as triangular, rectangular or square or any variation around these geometries.

The term "Needle Cannula" is used to describe the actual conduit performing the penetration of the skin during injection. A needle cannula is usually made from a metallic material such as e.g. stainless steel, but could also be made from a polymeric material or a glass material.

As used herein, the term "liquid drug" is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

The term "preservative containing liquid drug" is meant to encompass any liquid drug containing any amount of a preservative. The preservative used in drugs are often meta-cresol or phenol but could be any kind of preservative.

"Cartridge" is the term used to describe the container actually containing the drug. Cartridges are usually made from glass but could also be moulded from any suitable polymer. A cartridge or ampoule is preferably sealed at one end by a pierceable membrane referred to as the "septum" which can be pierced e.g. by the non-patient end of a needle cannula. Such septum is usually self-sealing which means that the opening created during penetration seals automatically by the inherent resiliency once the needle cannula is removed from the septum. The opposite end is typically closed by a sealing member such as a plunger or piston made from rubber or a suitable polymer. The plunger or piston can be slidable moved inside the cartridge. The space between the pierceable membrane and the movable plunger holds the drug which is pressed out as the plunger decreased the volume of the space holding the drug. However, any kind of container rigid or flexible can be used to contain the drug.

Since a cartridge usually has a narrower distal neck portion into which the plunger cannot be moved not all of the liquid drug contained inside the cartridge can actually be expelled. The term "initial quantum" or "substantially used" therefore refers to the injectable content contained in the cartridge and thus not necessarily to the entire content.

"Cleaning chamber" is in the present description broadly meant to be any kind of reservoir containing a cleaning solvent to clean at least the distal tip of the needle cannula between subsequent injections. Such cleaning chamber is preferably both distally and proximally sealed by a pierceable septum. However, the pierceable septum could be replaced by any kind of sealing which would seal against the outer surface of the needle cannula. The distal septum and the proximal septum or seal of the cleaning chamber defines a confinement containing the cleaning solvent which cleaning solvent in a preferred embodiment is identical to the preservatives contained in the liquid drug used in the specific injection device. In a most preferred solution, the same preservative containing liquid drug is present in both the cleaning chamber and in the cartridge of the injection device thereby avoiding contamination of the preservative containing drug inside the cartridge.

By the term "Pre-filled" injection device is meant an injection device in which the cartridge containing the liquid drug is permanently embedded in the injection device such that it cannot be removed without permanent destruction of the injection device. Once the pre-filled amount of liquid drug in the cartridge is used, the user normally discards the entire injection device. This is in opposition to a "Durable" injection device in which the user can himself change the cartridge containing the liquid drug whenever it is empty. Pre-filled injection devices are usually sold in packages containing more than one injection device whereas durable injection devices are usually sold one at a time. When using pre-filled injection devices an average user might require as many as 50 to 100 injection devices per year whereas when using durable injection devices one single injection device could last for several years, however, the average user would require 50 to 100 new cartridges per year.

Using the term "Automatic" in conjunction with injection device means that, the injection device is able to perform the injection without the user of the injection device delivering the force needed to expel the drug during dosing. The force is typically delivered—automatically—by an electric motor or by a spring drive. The spring for the spring drive is usually strained by the user during dose setting, however, such springs are usually prestrained in order to avoid problems of delivering very small doses. Alternatively, the spring can be fully preloaded by the manufacturer with a preload sufficient to empty the entire drug cartridge though a number of doses. Typically, the user activates a latch mechanism e.g. in the form of a button on, e.g. on the proximal end, of the injection device to release fully—or partially—the force accumulated in the spring when carrying out the injection.

The term "Permanently connected" or "permanently embedded" as used in this description is intended to mean that the parts, which in this application is embodied as a cartridge permanently embedded in the housing, requires the use of tools in order to be separated and should the parts be separated it would permanently damage at least one of the parts.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

When in the following terms as "upper" and "lower", "right" and "left", "horizontal" and "vertical", "clockwise" and "counter clockwise" or similar relative expressions are used, these only refer to the appended figures and not to an actual situation of use. The shown figures are schematic representations for which reason the configuration of the different structures as well as there relative dimensions are intended to serve illustrative purposes only.

In that context it may be convenient to define that the term "distal end" in the appended figure is meant to refer to the end of the injection device which points towards the skin of the user upon injection and which usually carries the injection needle whereas the term "proximal end" is meant to refer to the opposite end of the injection device which usually carries the dose setting button. "Distal" and "proximal" are meant to be along an axial orientation extending along the longitudinal axis of the injection device and is further indicated in the figures.

Figures 1, 2:
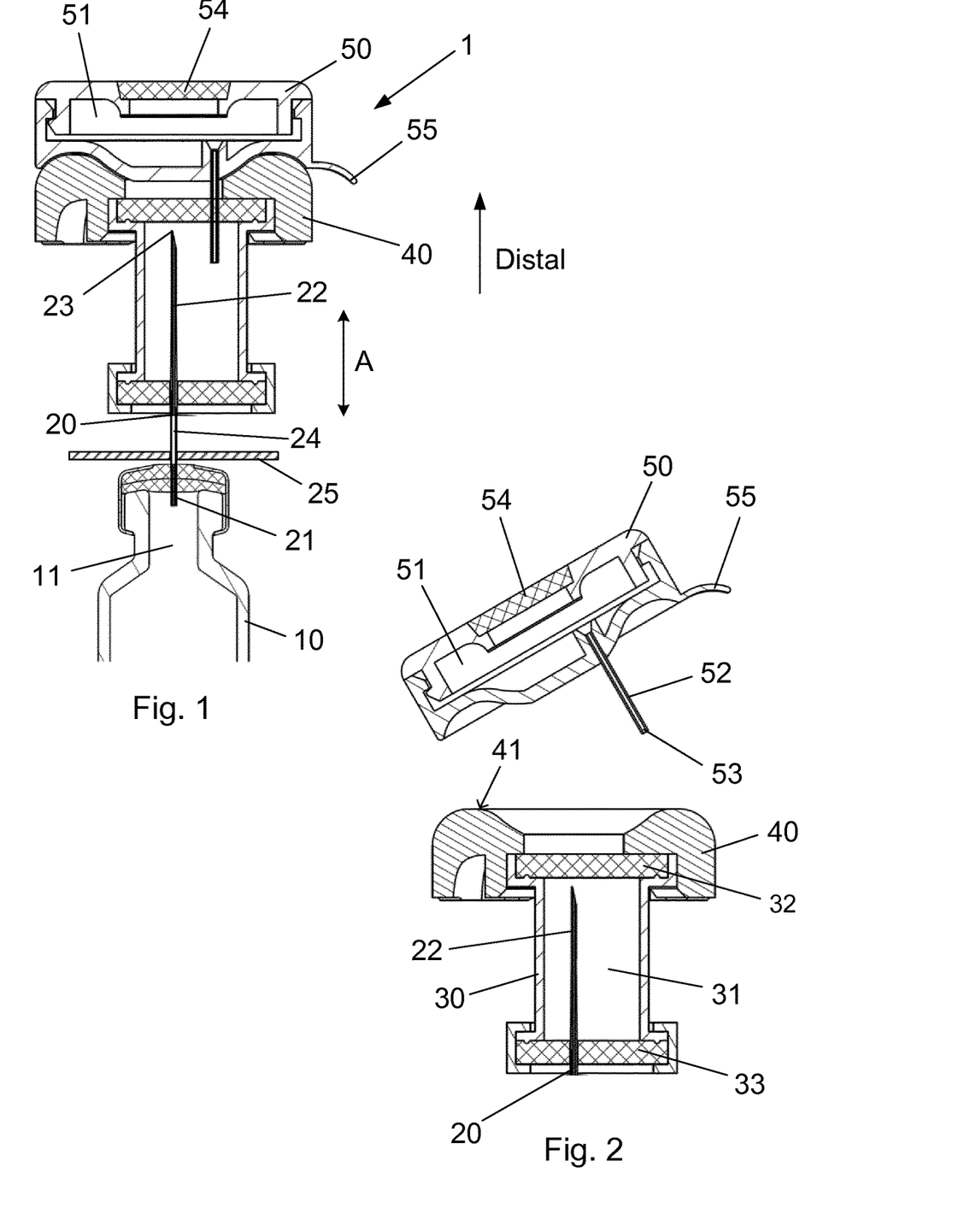
FIG. 1 show a cross-sectional view of the distal end of the injection device according to a first example of the invention during filling of the cleaning reservoir.
FIG. 2 show a cross-sectional view of the distal end of a pen shaped injection device of FIG. 1 when removing the distal cover after filling for sealing the cleaning reservoir.

Embodiment 1, FIG. 1-2

FIGS. 1 and 2 schematically discloses the distal end of a pen shaped injection device 1. A not shown housing supports a cartridge 10 which is filled with the liquid drug to be injected.

In order to facilitate the injection, a needle cannula 20 is provided with a proximal part 21 penetrated into the cartridge 10 and a distal part 22 with a distal tip 23 to be penetrated through the skin of a user during injection. The surface of the skin of the user is generally symbolized by an "S" in the following.

Between injections, the distal part 22 or at least the distal tip 23 is maintained inside a cleaning reservoir 31 which is carried by an axially movable shield 40. This movable shield 40 is moved in the proximal direction during injection and the injection itself can be spring driven by a spring engine which is released to drive out a set dose of the liquid drug from the cartridge 10 in response to a proximal movement of the movable needle shield As can be seen from FIG. 1, the lumen 24 of the needle cannula 20, at least between injections, creates a liquid communication between the interior 11 of the cartridge 10 and the cleaning reservoir 31.

This liquid communication is used to pump liquid drug into the cleaning reservoir 31. The injection device 1 is usually delivered to the user with an empty and sterile cleaning reservoir 31. Upon initiation of the injection device 1, a predetermined quantum of the liquid drug is pumped from the cartridge 10 and into the cleaning reservoir 31 such that the preservative present in the liquid drug is used for cleaning the distal tip 23 of the needle cannula 20 between injections. However, when filling liquid drug into the cleaning reservoir 31, the air trapped in the cleaning reservoir 31 must be able to escape as must any surplus of liquid drug filled into the cleaning reservoir 31.

The shield 40 is telescopically movable in relation to the not shown housing and to the cartridge 10 as indicated by the arrow "A". Further, the needle cannula 20 is secured in a hub 25 or by similar means which again is secured to the not shown housing, either permanently or removable. The needle cannula 20 could also be permanently and directly secured to the housing without the use of a hub 25.

The cleaning reservoir 31 is made from a longitudinal tube 30 carried by the axially movable shield 40 and sealed distally by a distal septum 32 to be pierced by the distal tip 23 of the needle cannula 20 during injection and proximally by a proximal septum 33 through which the needle cannula 20 is penetrated. These septum 32, 33 can be replaced by any kind of sealing which seals to the outer surface of the needle cannula 20.

Most distally the axially movable shield 40 is closed by a removable cover 50 which contains a hollow space 51 having a tube 52 with a lumen 53 extending in a proximal direction. The tube 52 can be either flexible or rigid.

This tube 52 is penetrated through the distal septum 32 and into the cleaning reservoir 31 such that liquid communication is also established between the cleaning reservoir 31 and the hollow space 51 of the removable cover 50.

Alternatively, the tube 52 could lead to directly to the surroundings without the presence of any chamber. If the tube 52 leads directly to the free some other sterilizations means could be provided.

When a user fills the cleaning reservoir 31 with liquid drug from the cartridge 10 preferably by pumping liquid drug from the interior 11 of the cartridge 10 and into the cleaning reservoir 31 both air and any surplus of liquid drug pumped will escape through the lumen 53 of the tube 52 and thus flow into the hollow space 51 (or alternatively simply to the surroundings). As a result, any over-pressure build-up inside the cleaning reservoir 31 is equalized through the lumen 53 of the tube 52 and the hollow space 51 acting as an overflow chamber.

Distally the removable cover 50 is provided with a transparent area 54 through which the user can inspect the filling of the hollow space 51. During filling of the cleaning reservoir 31, any presence of liquid drug inside the hollow space 51 indicates to the user that the cleaning reservoir 31 has been properly filled.

Hereafter, the user can simply remove the removable cover 50 by pulling away the tab 55 as disclosed in FIG. 2 where after the injection device 1 is ready for use. For reason of simplicity, the cartridge 10 is not depicted in FIG. 2.

The cover 50 could in one example be a part of a protective cap covering the distal part of the injection device 1 such that the cover 50 is automatically pulled away when the cap is removed to perform an injection.

After removable of the cover 50, the injection is performed by pressing the distal surface 41 of the axially movable shield 40 against the body of the user such that the distal tip 23 of the needle cannula 20 penetrates through the distal septum 32 and into the skin of the user. The injection itself can be performed automatically or manually.

Figure 3:
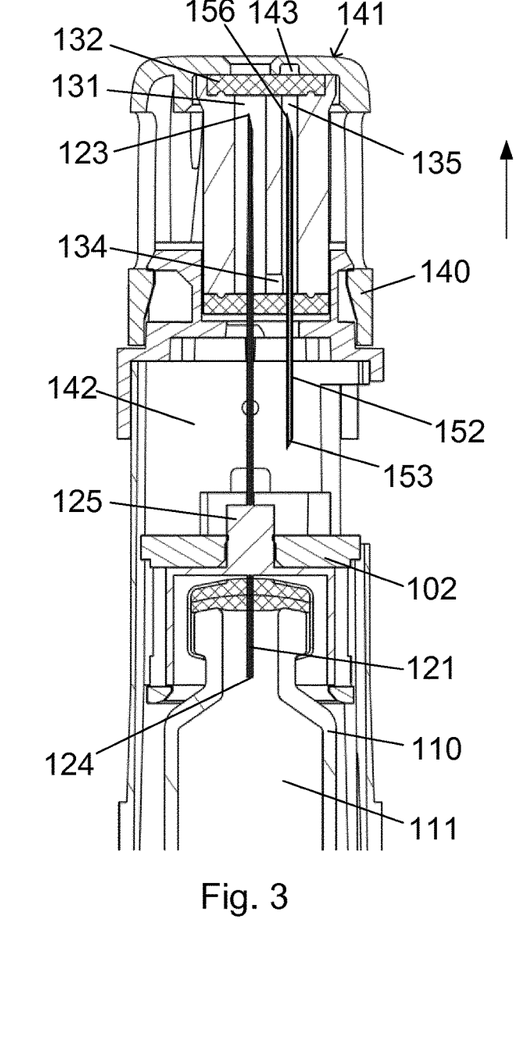
FIG. 3 show a cross-sectional view of the distal end of the injection device according to a second example during filling of the cleaning reservoir.
Figure 4:
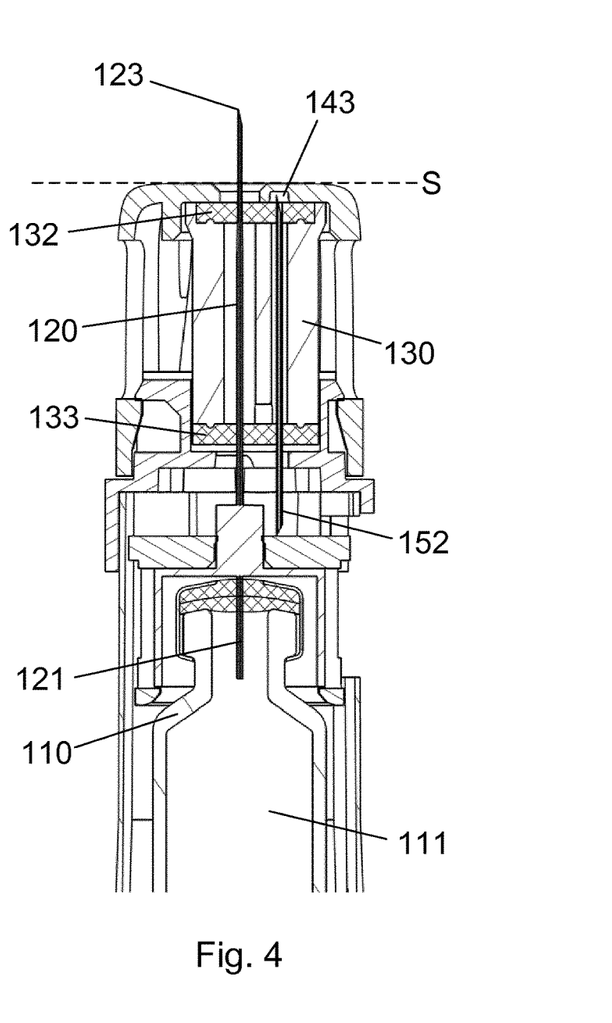
FIG. 4 show a cross-sectional view of the distal end of the injection device of FIG. 3 during initial injection.
Figure 5:
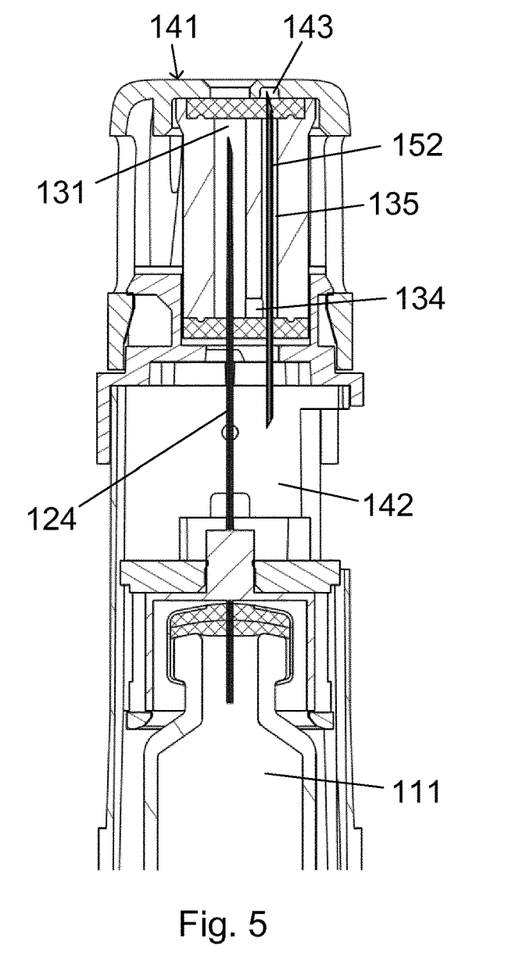
FIG. 5 shows a cross-sectional view of the distal end of the injection device of FIG. 3 following an initial injection.

Embodiment 2, FIG. 3-5

A different embodiment is disclosed in the FIGS. 3 to 5 wherein similar elements are numbered by the same reference numbers however with a "1" in front of the number.

As seen in FIG. 3, the needle cannula 120 is secured in a hub 125 which is attached to the housing 102 either permanently or removable, housing a cartridge 110 having contents 111.

When the user pumps liquid drug through the lumen 124 of the needle cannula 121/120 and into the cleaning reservoir 131 as disclosed in FIG. 3 air and any surplus of liquid drug will flow through the radial opening 134 and into a parallel chamber 135 provided in the tube 130. Via this parallel chamber 135, the liquid drug will flow through the lumen 153 of the tube 152 and into an overflow chamber 142 provided in the axially movable shield 140 henceforth any pressure being build up inside the cleaning reservoir 131 during filling is quickly equalized.

The filling of the cleaning reservoir 131 is preferably done automatically when preparing the injection device for injection e.g. by being coupled to the removal of the protective cap from the housing of the injection device.

When an injection is being performed as disclosed in FIG. 4, the distal surface 141 of the axially movable shield 140 is pressed against the skin of the user (indicated by "S" in FIG. 4) thus the distal tip 123 of the needle cannula 120 penetrates through the distal septum 132 (and proximally by a proximal pierceable seal 133) and into the skin ("S") of the user as illustrated in FIG. 4.

At the same time the distal end 156 of the tube 152 also penetrates through the distal septum 132 and into a chamber 143 provided in the axially movable shield 140 (see FIG. 4). The cleaning reservoir 131 is thus sealed by this action.

The various frictions are thus designed such that the tube 152 remains in this position i.e. with the distal end 156 inserted into the sealed chamber 143 thereby rendering the overflow escape route closed.

When the injection is finished and the user removes the axial movable shield 140 from the skin ("S"), the axially movable shield 140 is urged in the distal direction by a not shown compression spring which preferably is incorporated between the housing and the axially movable shield 140. Once the axial movable shield 140 returns to the initial position as disclosed in FIG. 5, the distal end 156 of the tube 150 is maintained inside the sealed chamber 143.

It is thus possible to fill the cleaning reservoir 131 such that any air and surplus which would build up an overpressure inside the cleaning reservoir 131 is transferred to the overflow chamber 142. During the first injection, the liquid communication between the cleaning reservoir 131 and the overflow chamber 142 is closed such that the cleaning reservoir 131 hereafter is permanently sealed.

Embodiment 3, FIG. 6-10

A further embodiment is disclosed in the FIGS. 6 to 10. In this third embodiment, similar elements are numbered using the same reference numbers with a "2" in front.

Figure 6:
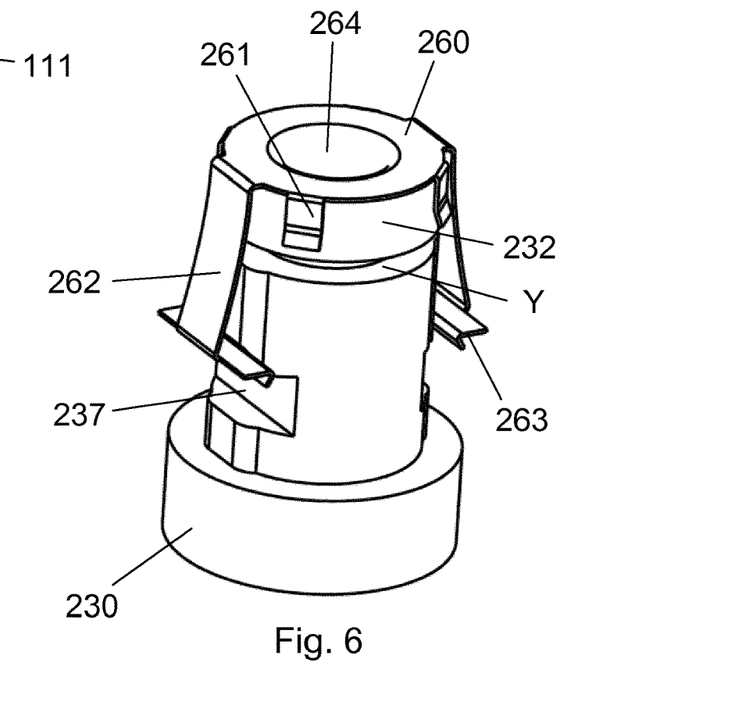
FIG. 6 show a perspective view of the distal end of the injection device according to a third example during filling of the cleaning reservoir.

A perspective view of the distal part of the tube 230 is disclosed in FIG. 6. The tube 230 is carried by the axial movable shield as in the first embodiment. The distal septum 232 is in the initial position axially removed from the tube 230 such that a gap "Y" is provided between the tube 230 and the distal septum 232. This is probably best seen in FIG. 7.

The distal septum 232 is carried by a metallic clip 260 which has a number of proximally pointing short arms 261 securing the distal septum 232 to the metallic clip 260 and a number of longer arms 262 securing the metallic clip 260 to the tube 230 by way of channel 237. Centrally the metallic clip 260 is provided with an opening 264 through which the distal tip 223 of the needle cannula 220 penetrates during injection. The longer arms 262 are in the initial position which is depicted in FIGS. 6 and 7 bended radially outwardly by the tube 230 and is proximally provided with hooks 263.

Further, the tube 230 is on the outside surface provided with a number of indentations 243 into which the hooks 263 of the metallic spring 260 fits as will be explained.

Figure 7:
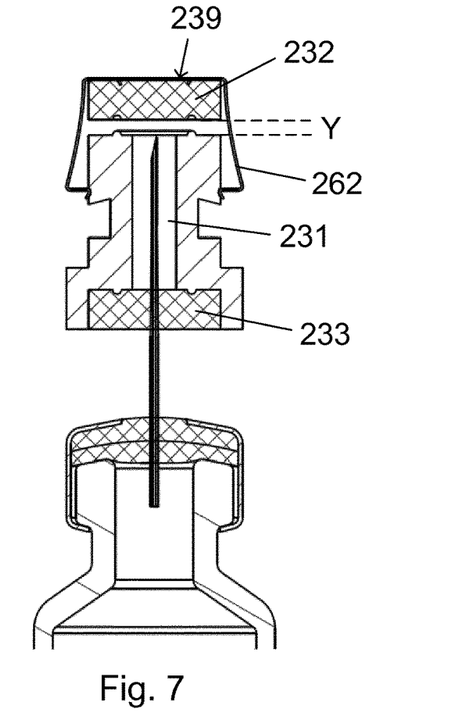
FIG. 7 show a cross sectional view of FIG. 6.
Figure 8:
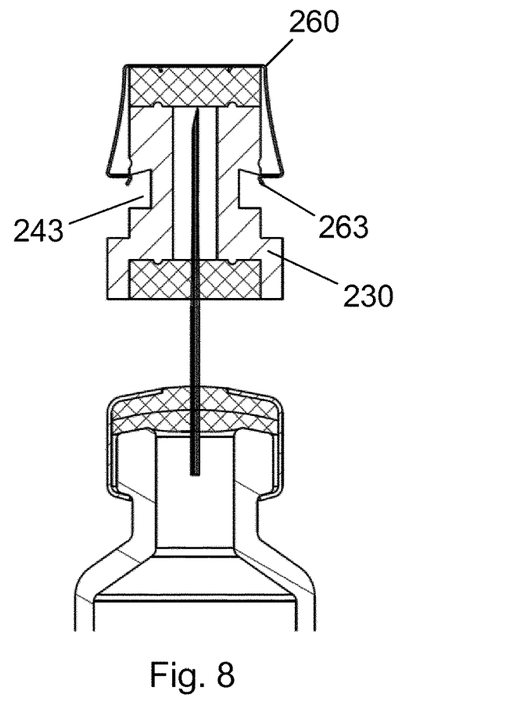
FIG. 8 show a cross-sectional view of the distal end of the injection device of FIG. 6 during sealing of the cleaning reservoir.

Prior to performing the first injection, the injection device 201 is delivered to the user with the distal septum 232 positioned the distance "Y" from the tube 230 as disclosed in FIG. 6 and FIG. 7.

As can be seen from FIG. 7, the cleaning reservoir 231 is proximally sealed by the proximal septum 233 and the distal tip 223 of the needle cannula 220 is located inside the cleaning reservoir 231.

When a user pumps liquid drug from the cartridge 210 and into the cleaning reservoir 231 (or it is done automatically) any air and surplus pumped can escape through the gap "Y" and no overpressure will be present inside the cleaning reservoir 231 after filling.

As the gap "Y" leads to the surroundings some kind of sterilize environment can be provided around the tube 230.

When a user performs the first injection, the distal surface 239 of the tube 230 (or the axially movable shield carrying the tube) is pressed against the skin of the user. This action moves the metallic clip 260 and thus the distal septum 232 in the proximal direction as disclosed in FIG. 8. Once the gap "Y" is closed, the hooks 263 of the metallic clip 260 engages the indentations 243 on the tube 230 thereby sealing the cleaning reservoir 231 as disclosed in FIG. 9.

Figure 9:
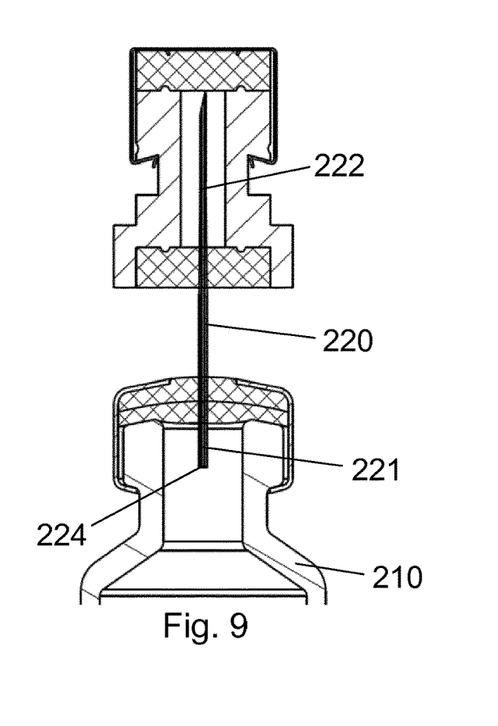
FIG. 9 show a cross-sectional view of the distal end of the injection device of FIG. 6 with the cleaning reservoir sealed.

FIG. 9 further shows a needle cannula 220 having a distal part 222 with a distal tip 223 (not shown in FIG. 9) and a proximal part 221 and a longitudinal lumen 224 there between, the needle cannula 220 being mounted relatively to the housing such that the distal part 222 extends in a distal direction and the proximal part 221 extends in a proximal direction and into the cartridge 210 at least during injection.

The action of moving the distal surface 239 of the axially movable shield 240 in the proximal direction can also be made from different means than performing an injection. Separate and independent means for moving the distal surface 239 of the tube 230 proximally could thus be provided.

Figure 10:
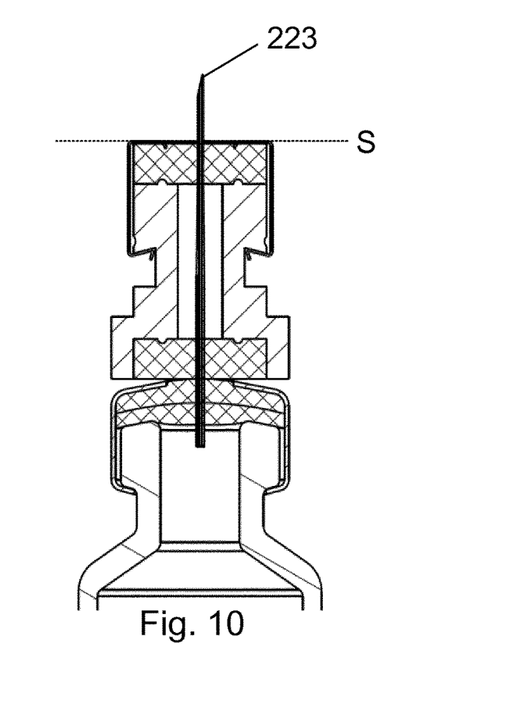
FIG. 10 show a cross-sectional view of the distal end of the injection device of FIG. 6 during injection.

As the user presses the distal surface 241 harder towards the skin, the distal tip 223 of the needle cannula 220 will penetrate through the distal septum 232 and into the skin "S" of the user to deliver the liquid drug as disclosed in FIG. 10.

Following the first injection a not shown compression spring urges the axially movable shield carrying the tube 230 with the cleaning reservoir 231 back to the initial position disclosed in FIG. 9 where after further injections can be performed with the distal tip 223 of the needle cannula 220 moving in and out of the now sealed cleaning reservoir 231.

In a further example relating to the FIGS. 6 to 10, the tube 230 could be inverted such that the septum herein designated to be the distal septum 232 abuts the injection device. The gap "Y" would in such example be located adjacent the cartridge 210.

Embodiment 4, FIG. 11-17

Yet a different embodiment is disclosed in the FIGS. 11 to 17. In this embodiment similar elements are numbered using the same reference numbers with a "3" in front.

Figure 11:
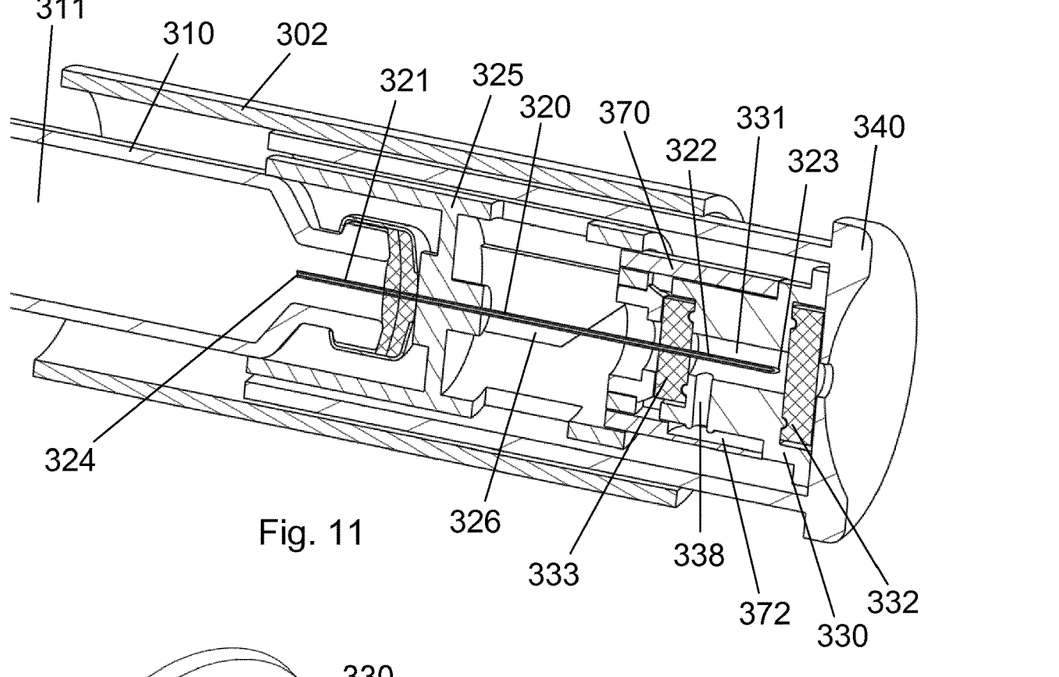
FIG. 11 show a perspective view of the distal end of the injection device according to a fourth example during filling of the cleaning reservoir.

The distal part of the pen-shaped injection device is disclosed in FIG. 11. The proximal part 321 of the needle cannula 320 having a distal part 322 is inserted into the interior 311 of the cartridge 310 and the distal tip 323 of the needle cannula 320 is provided inside the cleaning reservoir 331.

The needle cannula 320 which as in the previous embodiment has a longitudinal lumen 324 through which the liquid drug can flow is secured in a hub 325 as depicted in FIG. 11.

The cleaning reservoir 331 is made in the tube 330 wherein the distal end is sealed by a distal septum 332 and the proximal end is sealed by a proximal septum 333. The hollow tube 330 is carried by the axial movable shield 340 which is able to telescope in relation to the housing 302 and the cartridge 310 which is secured in the housing 302.

Figures 12, 13:
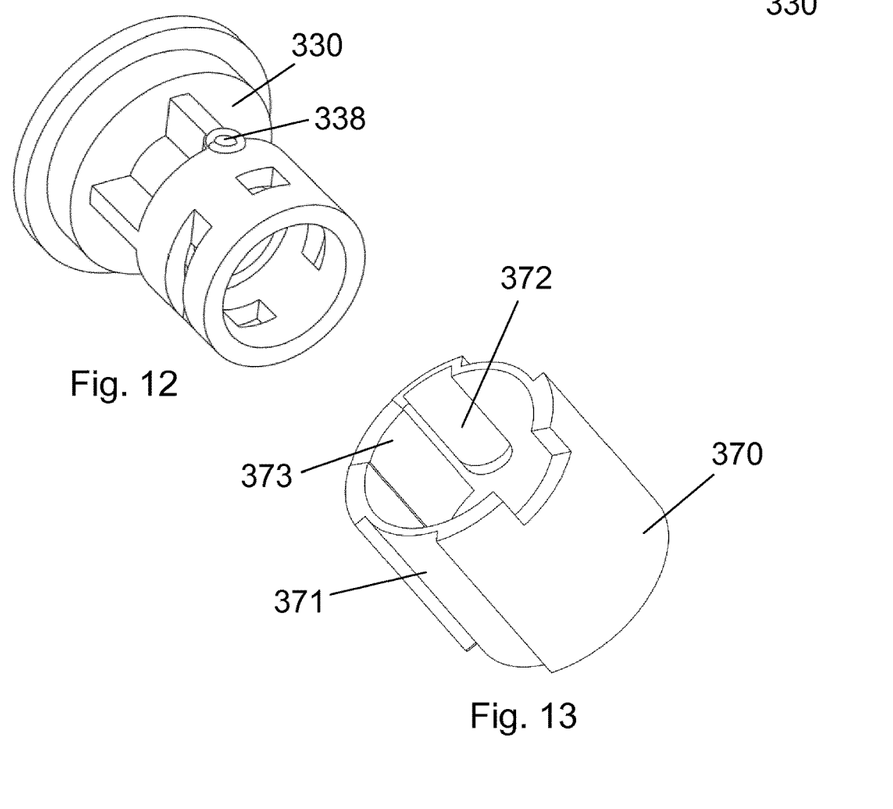
FIG. 12 show a perspective view of the tube part of the fourth embodiment.
FIG. 13 show a perspective view of the rotatable seal element of the fourth embodiment.

The tube 330 forming the cleaning reservoir 331 is further provided with a radial opening 338 through which air and liquid drug inside the cleaning reservoir 331 can escape such that when a user pumps liquid drug from the interior 311 of the cartridge 310 and through the lumen 324 of the needle cannula 320 and into the cleaning reservoir 231 any air and surplus liquid drug that is pumped is able to flow through this radial opening 338 thereby preventing an over-pressure from being maintained inside the cleaning reservoir 331.

Surrounding the hollow tube 330 is located a seal element 370 which is mounted such that the tube 330 and the seal element 370 is able to rotate in relation to each other. In the embodiment disclosed in the FIGS. 11 to 16, the seal element 370 is the rotatable part, however kinematic reversal would be possible such that the tube 330 could be the rotatable part.

This seal element 370 is on its outside surface provided with a longitudinal track 371, the use of which will be explained. On the inside surface a longitudinal recess 372 and a rubber seal 373 is provided.

Figure 14:
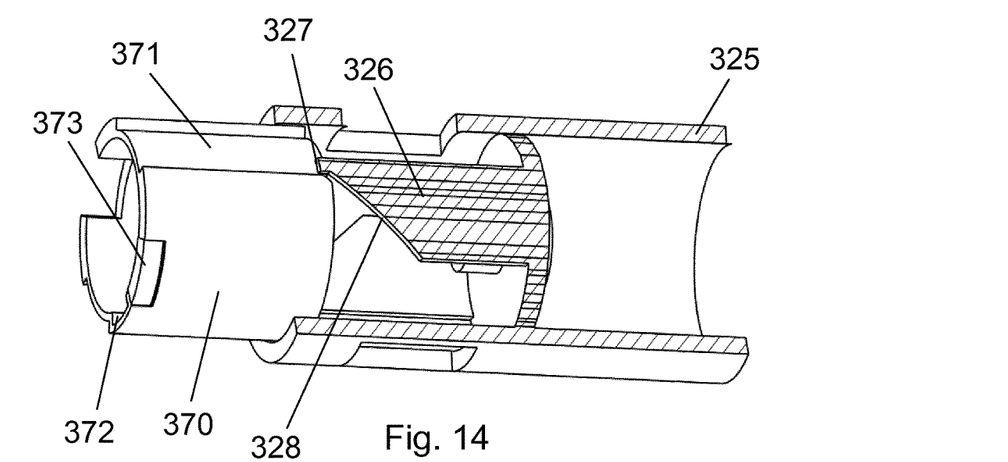
FIG. 14 Show a cut-open view of the engagement between the hub and the rotatable seal element during filling of the cleaning reservoir in the fourth example.
Figure 15:
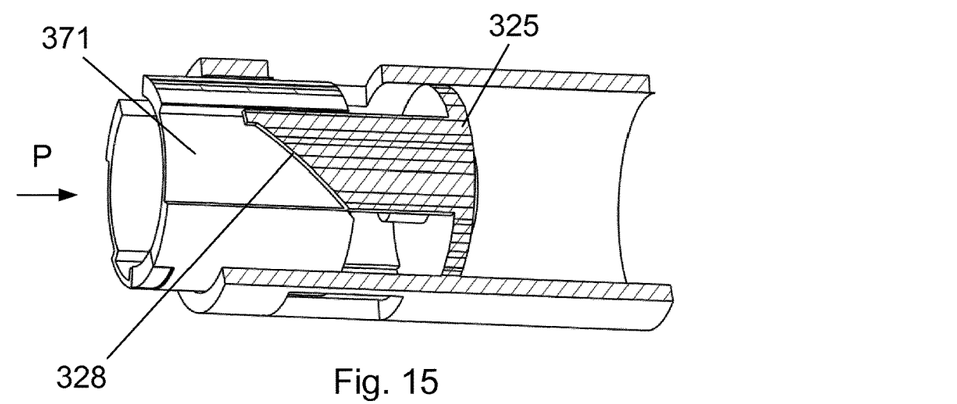
FIG. 15 Show a cut-open view of the engagement between the hub and the rotatable seal element during sealing of the cleaning reservoir in the fourth example.

The engagement between the hub 325 and the rotatable seal element 370 is further disclosed in FIGS. 14 and 15. The hub 325 is provided with a number (in this embodiment; two) uprights 326. These uprights 236 are provided on the periphery of the needle hub 325 and are distally provided with a nose 327 which connects to a sloped surface 328.

Figure 16:
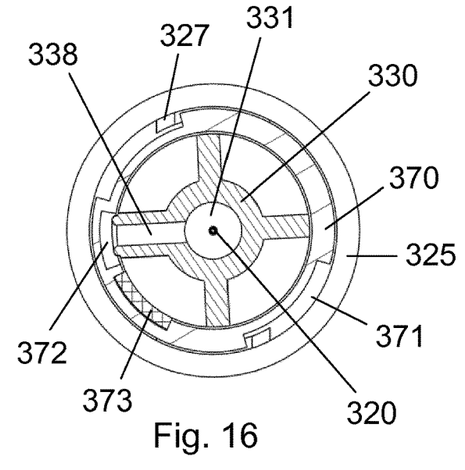
FIG. 16 show a view through FIG. 11 during filling of the cleaning reservoir.

FIG. 11, FIG. 14 and FIG. 16 depict the injection device in the same position in which liquid drug is pumped into the cleaning reservoir 331. As can be seen air and any surplus pumped can escape though the radial opening 338 and into the recess 372. In this position, the noses 327 on the uprights 326 of the hub 325 are located in the proximal part of the longitudinal tracks 371 of the rotatable seal element 370.

The recess 372 can in one example lead to the surroundings such that the pressure inside the cleaning reservoir can be equalized with the atmospheric pressure of the surroundings.

When the user performs the first injection indicated by the arrow "P" in FIG. 15, the tube 330 and the rotatable seal element 370 is moved proximally in relation to the hub 325. As the hub 325 is non rotational mounted, the sloped surface 328 of the uprights 326 forces the rotatable seal element 370 to rotate.

Figure 17:
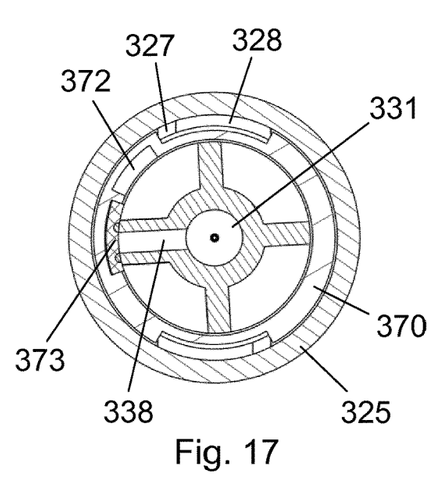
FIG. 17 show a view through FIG. 11 during sealing of the cleaning reservoir.

This rotation of the rotatable seal element 370 shifts the recess 372 away from radial opening 338 and brings the rubber seal 373 in front of the radial opening 338 thereby sealing the cleaning reservoir 330 as disclosed in FIG. 15 and in FIG. 17. The radial opening 338 can further be provided with sealing ribs that creates a tight compression against the rubber seal 373.

For the following injections, the rotatable seal element 370 maintains its rotational position such that the cleaning reservoir 331 is permanently sealed once the user has performed the initial injection. For that purpose, the rotatable seal element 370 can be provided with a non-shown one-way mechanism preventing further rotation once the rotatable seal element 370 has entered the rotational position disclosed in FIG. 15 and FIG. 17.

Figure 18:
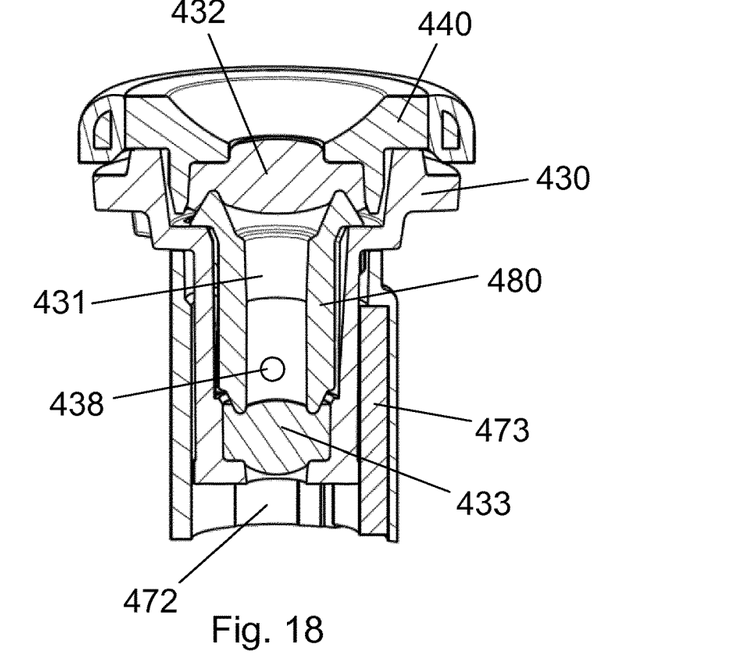
FIG. 18 show a cross sectional view of the cleaning unit attached to the axially movable shield according to a fifth example.
Figure 19:
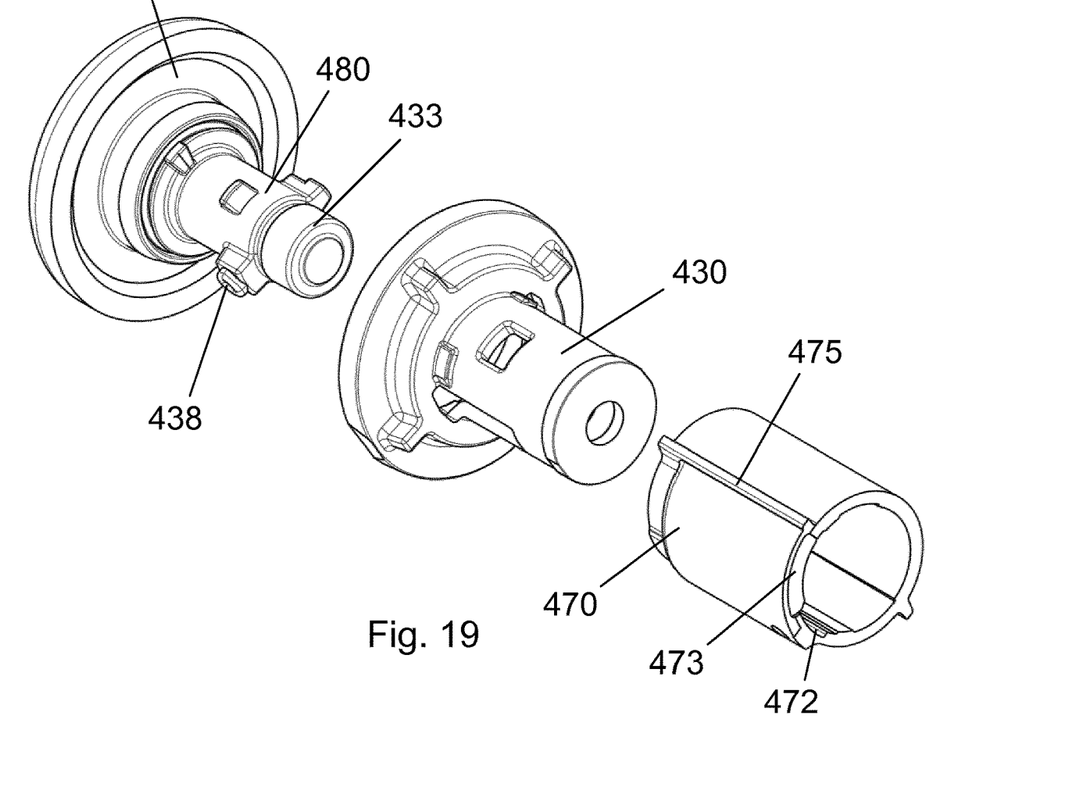
FIG. 19 show an exploded view of the cleaning unit of FIG. 18

Embodiment 5, FIG. 18-19

A further embodiment of a closing valve is disclosed in FIG. 18 and FIG. 19 in which similar elements are numbered using the same reference numbers with a "4" in front.

FIG. 18 discloses the cleaning unit which comprises a distal septum 432 and a proximal septum 433. These two septum 432, 433 are kept in the correct distance by a spacer element 480 and both septum 432, 433 and the spacer element 480 are secured in the tube 430. The tube 430 is preferably distally welded to the axial movable shield 440 such that the tube 430 moves together with the axial movable shield 440.

During manufacture when the shield 440 and the tube 430 are welded together a pressure is thus applied to the two septum 432, 433 and to the spacer element 480 such that a tight sealing is provided.

Both the tube 430 and the spacer element 480 are provided with a radial opening 438 through which air and any surplus liquid drug can escape during filling of the cleaning reservoir.

Surrounding the tube 430 is the seal element 470. As in the previous embodiment, the seal element 470 is provided with a longitudinal track 472 and a rubber seal 473.

When the injection device is delivered to the user the radial opening 438 point into the open longitudinal track 472 such that air and any surplus liquid drug can escape during filling of the cleaning reservoir 431.

The longitudinal track 472 can either be a closed track or it can lead out to the surroundings such that the pressure inside the cleaning reservoir is equalized with the atmospheric pressure of the surroundings.

During initiation of the injection device, the tube 430 and the seal element 470 are rotated relatively to each other such that the rubber seal 473 is brought into a position in which the rubber seal 473 covers the radial opening 438 thus sealing the cleaning reservoir 431.

In a specific embodiment disclosed in European Patent Application No.: EP16177273.6, the seal element 470 is rotational secured by the rib 475 whereas the shield 440 and the tube 430 are rotated during initiation. Once the radial opening 438 is sealed by rotation of the axially movable shield 440 and henceforth the tube 430, the tube 430 and the seal element 470 are locked to each other either by friction or by a not-shown click mechanism such that the radial opening 438 remains sealed during future injections.

Figure 20:
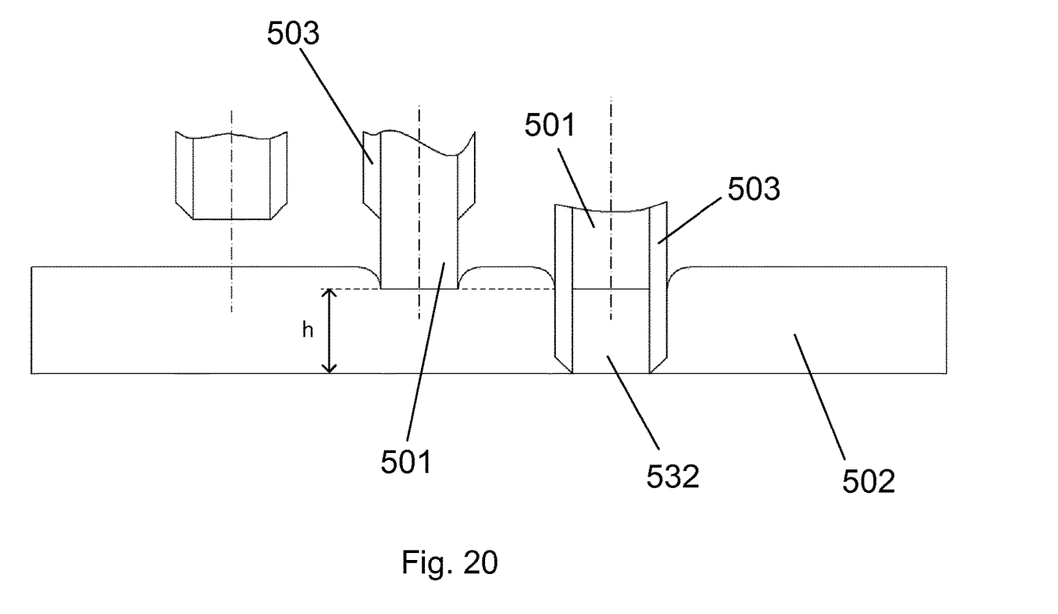
FIG. 20 show a schematic representation of a procedure for stamping out the septum for the cleaning unit.

The Septum, FIG. 20

As disclosed in FIG. 18, the two septum 432, 433 are pressed in the axial direction during assembly. When the septum 432, 433 are subject to an axial pressure the diameter will expand radially since the septum 432, 433 are made from an elastomeric material. In order to secure that sufficient space is available in the radial direction, the diameter has to be somewhat smaller than the diameter of the area of the compartment into which the septum are fitted.

In order to manufacture these septum 432, 433 a procedure as disclosed in FIG. 20 is used.

A first tool 501 is first used to press a part of an elastomeric plate 502 to the height "h" which equals the height the septum 432, 433 will have when press-mounted in the cleaning unit. After the first tool 501 has pressed the plate 502 to the height "h" a stamping tool 503 stamps out the septum 532 from the elastomeric plate 502.

Once the first tool 501 and the stamping tool 503 are retracted, the septum 532 will expand in the axial direction to the initial height of the elastomeric plate 502. However, when expanding, the diameter will retract radially such that it now fits in to compartment in which it is supposed to be placed.

Some preferred embodiments have been shown in the foregoing, but it should be stressed that the invention is not limited to these, but may be embodied in other ways within the subject matter defined in the following claims.

The invention claimed is:

1. A medical injection device for apportioning doses of a preservative containing liquid drug, comprising:
a housing supporting a cartridge containing the preservative containing liquid drug,
a needle cannula having a distal part with a distal tip and a proximal part and a longitudinal lumen there between, the needle cannula being mounted relatively to the housing such that the distal part extends in a distal direction and the proximal part extends in a proximal direction and into the cartridge at least during injection,
an axial movable shield which is axially movable in relation to the housing from a first position to a second position and which axial movable shield carries a cleaning reservoir which distally is sealed by a distal pierceable seal and proximally by a proximal pierceable seal longitudinally spaced from each other and which cleaning reservoir is filled with an amount of the preservative containing liquid drug, wherein the distal tip of the needle cannula in the first position is located inside the cleaning reservoir and in the second position is located distal to the cleaning reservoir,
wherein the cleaning reservoir has an outlet such that the preservative containing liquid drug can escape from the cleaning reservoir during filling of the cleaning reservoir and which injection device further is provided with a sealing structure or first seal element for sealing the outlet, such that further preservative containing liquid drug is prevented from escaping from the cleaning reservoir.

2. The medical injection device according to claim 1, wherein the sealing structure or first seal element for sealing the outlet is configured to be activated by a user operation.

3. The medical injection device according to claim 1, wherein the outlet terminates in an overflow chamber.

4. The medical injection device according to claim 3, wherein the cleaning reservoir and the overflow chamber are connected by a tube having a lumen.

5. The medical injection device according to claim 1, wherein the outlet terminates in an overflow chamber.

6. The medical injection device according to claim 5, wherein the cleaning reservoir and the overflow chamber are connected by a tube having a lumen.

7. The medical injection device according to claim 6, wherein the axial movable shield is provided with a removable part comprising a sealing structure or seal element.

8. The medical injection device according to claim 1, wherein the outlet connects the cleaning reservoir to an overflow channel via a radial opening.

9. The medical injection device according to claim 8, wherein the radial opening is sealable by a second seal element.

10. The medical injection device according to claim 9, wherein a tube structure comprising the cleaning reservoir is surrounded by the second seal element.

11. The medical injection device according to claim 9, wherein a tube structure and the second seal element are rotatable in relation to each other.

12. The medical injection device according to claim 11, wherein the second seal element and the tube structure are rotationally locked following relative rotation.

13. The medical injection device according to claim 1, wherein the cleaning reservoir is configured as a tube structure distally sealed by the distal pierceable seal and proximally sealed by the proximal pierceable seal and which tube structure is carried by the axial movable shield.

14. The medical injection device according to claim 13, wherein the outlet terminates into the surroundings.

15. The medical injection device according to claim 14, wherein the proximal pierceable seal is distally removed a distance (Y) from the tube structure.

16. The medical injection device according to claim 15, wherein the cleaning reservoir is sealed by moving the proximal pierceable seal the removed distance (Y) towards the tube structure.

17. The medical injection device according to claim 14, wherein the distal pierceable seal is distally removed a distance (Y) from the tube structure.

18. The medical injection device according to claim 17, wherein the cleaning reservoir is sealed by moving the distal pierceable seal the removed distance (Y) towards each other.

19. A medical injection device for apportioning doses of a preservative containing liquid drug, comprising:
a housing supporting a cartridge containing the preservative containing liquid drug,
a needle cannula having a distal part with a distal tip and a proximal part and a longitudinal lumen there between, the needle cannula being mounted relatively to the housing such that the distal part extends in a distal direction and the proximal part extends in a proximal direction and into the cartridge at least during injection,
an axial movable shield which is axially movable in relation to the housing from a first position to a second position and which axial movable shield carries a cleaning reservoir which distally is sealed by a distal pierceable seal and proximally by a proximal pierceable seal longitudinally spaced from each other and which cleaning reservoir is filled with an amount of the preservative containing liquid drug, wherein the distal tip of the needle cannula in the first position is located inside the cleaning reservoir and in the second position is located distal to the cleaning reservoir,
wherein the cleaning reservoir has an outlet such that the preservative containing liquid drug can escape from the cleaning reservoir during filling of the cleaning reservoir and which injection device further is provided with a sealing structure or first seal element for sealing the outlet, such that further preservative containing liquid drug is prevented from escaping from the cleaning reservoir,
wherein the cleaning reservoir further being configured as a tube structure distally sealed by the distal pierceable seal and proximally sealed by the proximal pierceable seal and which tube structure is carried by the axial movable shield,
wherein the outlet connects the cleaning reservoir to an overflow channel via a radial opening which is sealable by a second seal element, and the tube structure comprising the cleaning reservoir is surrounded by the second seal element, wherein the tube structure and the second seal element are rotatable in relation to each other,
such that the second seal element can be brought to a sealed position by a relative rotation between the cleaning reservoir and the second seal element.

20. The medical injection device according to claim 19, wherein the sealing structure or first seal element for sealing the outlet is configured to be activated by a user operation.

21. The medical injection device according to claim 19, wherein the second seal element and the tube structure are rotationally locked following relative rotation.

22. The medical injection device according to claim 19, wherein the outlet terminates into the surroundings.

23. The medical injection device according to claim 22, wherein the proximal pierceable seal is distally removed a distance (Y) from the tube structure.

24. The medical injection device according to claim 22, wherein the distal pierceable seal is distally removed a distance (Y) from the tube structure.

25. The medical injection device according to claim 24, wherein the cleaning reservoir is sealed by moving the distal pierceable seal the removed distance (Y) towards the tube structure.

26. The medical injection device according to claim 24, wherein the cleaning reservoir is sealed by moving the proximal pierceable seal the removed distance (Y) towards the tube structure.

\* \* \* \* \*

UNITED STATES PATENT AND TRADEMARK OFFICE
CERTIFICATE OF CORRECTION

| | |
|---|---|
| PATENT NO. | : 11,052,185 B2 |
| APPLICATION NO. | : 15/757931 |
| DATED | : July 6, 2021 |
| INVENTOR(S) | : Larsen et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 448 days.

Signed and Sealed this
Twenty-fifth Day of February, 2025

Coke Morgan Stewart
*Acting Director of the United States Patent and Trademark Office*